United States Patent [19]

Bailly

[11] Patent Number: 4,469,740
[45] Date of Patent: Sep. 4, 1984

[54] FOAM PLASTIC MATERIAL WITH MOISTURE REMOVING PROPERTIES

[76] Inventor: Richard L. Bailly, Beechwood Cir., Boxford, Mass. 01921

[21] Appl. No.: 544,500

[22] Filed: Oct. 24, 1983

Related U.S. Application Data

[63] Continuation-in-part of Ser. No. 470,606, Feb. 28, 1983.

[51] Int. Cl.³ .............................................. B32B 3/06
[52] U.S. Cl. .................................... 428/212; 156/148; 428/234; 428/300; 428/314.4; 428/316.6
[58] Field of Search ............... 428/212, 234, 235, 300, 428/316.6, 314.4; 156/148

[56] References Cited

U.S. PATENT DOCUMENTS

| | | | |
|---|---|---|---|
| 3,545,442 | 12/1970 | Wicker et al. | 128/296 |
| 3,842,519 | 10/1974 | Lapidus | 36/44 |
| 3,852,897 | 12/1974 | Bridge | 36/44 |
| 3,882,857 | 5/1975 | Woodall, Jr. | 128/90 |
| 4,062,131 | 12/1977 | Hsiung | 36/44 |
| 4,076,019 | 2/1978 | Sain | 128/83 |
| 4,099,342 | 7/1978 | Singh | 36/44 |
| 4,108,169 | 8/1978 | Parker | 128/89 R |
| 4,137,110 | 1/1979 | Singh | 156/62.2 |
| 4,185,402 | 1/1980 | Digate | 36/44 |
| 4,186,499 | 2/1980 | Massok et al. | 36/44 |
| 4,192,086 | 3/1980 | Sichak | 36/44 |
| 4,197,343 | 4/1980 | Forsythe | 428/300 |
| 4,199,639 | 4/1980 | Ronc | 428/300 |
| 4,223,458 | 9/1980 | KIhara | 36/44 |
| 4,235,027 | 11/1980 | Singh | 36/44 |
| 4,250,172 | 2/1981 | Mutzenberg | 428/234 |
| 4,257,176 | 3/1981 | Hartung et al. | 36/44 |
| 4,306,549 | 12/1981 | Canie | 128/90 |
| 4,323,061 | 4/1982 | Usukura | 128/90 |
| 4,424,248 | 1/1984 | Tesch et al. | 428/300 |
| 4,426,414 | 1/1984 | Wilkerson | 428/300 |

FOREIGN PATENT DOCUMENTS 2651089 5/1978 Fed. Rep. of Germany ...... 335/128

Primary Examiner—William J. Van Balen
Attorney, Agent, or Firm—Lahive & Cockfield

[57] ABSTRACT

A material is formed by needling a layer of hydrophobic fibers into one face of a layer of closed-cell, foamed, thermoformable plastic, and needling a layer of hydrophilic fibers into the opposite face so that the hydrophobic fibers and the hydrophilic fibers overlap within the foam. The material may be thermoformed to produce articles having a surface shape conforming to the contours of a region of the human body such as resilient supportive innersoles, soft casts or splints, and impact-absorbing pads. Such articles, in addition to their usual function, wick perspiration and moisture away from the skin.

15 Claims, 5 Drawing Figures

FOAM PLASTIC MATERIAL WITH MOISTURE REMOVING PROPERTIES

REFERENCE TO RELATED APPLICATIONS

This application is a continuation-in-part of U.S. application Ser. No. 470,606 filed Feb. 28, 1983 entitled Molded Odor-Absorbing Laminate.

BACKGROUND

This invention relates to improved materials for use in fabricating articles used in close contact with the human body such as impact-absorbing pads, innersoles, casts and splints, and other articles which are exposed to body perspiration. More particularly, the invention relates to a laminate-like material having a surface conforming to the contours of a selected region of the body which wicks perspiration or other moisture away from the body.

In the application of which this is a continuation-in-part, a laminate including an odor absorbing layer was disclosed. The invention disclosed herein does not include an odor absorbing layer but rather relies on overlapping hydrophobic and hydrophilic fibers, needled into a middle foam layer from opposite sides, to wick away perspiration and other moisture.

It has long been a goal to provide various products used on the body with the capacity to minimize the undesirable effects of body perspiration, moisture and associated odor. Clothing and shoes, for example, often include design features, fabrics, and materials directed to dispersing uncomfortable moisture from body surfaces. Polypropylene and other synthetic, hydrophobic fabrics are currently used in undergarments designed for wear during athletic activity because such fabrics are good insulators and wick perspiration away from the body.

There have been efforts to use the effects of hydrophobic fibers and hydrophilic fibers in materials applied to the body, for example, in U.S. Pat. No. 3,454,442 and German Pat. No. 2,651,089. However, none of these deal with the peculiar problems of molding structures that have a closed-cell foamed plastic layer, and, generally, the laminates shown can be improved greatly in their capacities for dispersing perspiration.

Accordingly, it is an object of this invention to provide a light-weight material that is sturdy, has enhanced moisture-wicking qualities, and is comfortable when maintained in direct contact with the human body. Another object is to provide a material which may be molded to form products for use on the body, such as shoe insoles, casts, impact absorbing pads, and similar products.

SUMMARY OF THE INVENTION

The invention in its broadest aspects comprises a trilayered laminate-like material designed for molding to form products used in contact with the human body. The material is used to fabricate, for example, innersoles, devices for immobilizing portions of the body during healing or therapy such as casts or splints, pads for impact-absorption such as are used on the interior of athletic wear for contact sports, low density thermally-insulating innerwear suitable for use in cold climates, and other articles. Products made in accordance with the process disclosed herein may be designed to exploit properties characteristic of foam plastic materials such as impact-absorption, water-repellance, thermal-insulating properties, and resilient or cushioned support. They are exceptionally comfortable when maintained in contact with the body for extended periods because of a soft inner layer that wicks perspiration away from the skin and an outer layer that disperses the perspiration passed through the normally moisture-impermeable foam.

These features are achieved by providing a material having at least one surface conforming substantially to the contours of a surface region of the human body, e.g., the sole of the foot, a shoulder, etc. The laminate comprises (1) a foamed thermoplastic middle layer, preferably closed-cell, with a thermoformed inner surface conforming to the contours of a region of the body, (2) a layer of hydrophobic fibers of polypropylene, polyester, or the like, needle punched into one side of the middle layer, which form a substantially continuous non-woven soft layer defining a multiplicity of interstitial spaces which act as air pockets and paths for wicking perspiration away from the skin, and (3) a layer of hydrophilic fibers needle punched into the other side of the middle layer so that the hydrophilic fibers overlap the hydrophobic fibers within the foam, for dispersing the perspiration.

In preferred embodiments, the material takes the form of a shock absorbing pad for use in athletic wear or the like or an innersole for footwear molded to fit within, for example, an athletic shoe or boot. The innersole has an upper thermoformed surface conforming to the surface shape of the human sole including an arch support and heel cup. In other embodiments, the material takes the form of a "soft cast", splint, or pad.

The products of the invention may be manufactured by placing a layer of hydrophobic fibers atop the foamed, thermoformable plastic middle layer, needle-punching the hydrophobic fibes to form an innermost layer, placing a layer of hydrophilic fibers atop the other side of the foamed middle layer, and needle-punching the hydrophilic fibers to form an outermost layer. The lengths of the hydrophobic and hydrophilic fibers and the depth of the needle punching operation are selected such that the hydrophobic and hydrophilic fibers overlap within the foam matrix. The material is then thermoformed by applying heat to the foamed layer to soften it and then imposing a surface contour to at least one surface, e.g., in a cooled mold. By selecting a suitable foamed plastic material such as the closed cell, cross-linked ethylene vinyl acetate or polyethylene foam, it is possible to shape the heated material directly about a body part such as an arm, leg, or ankle to form a soft cast. The overlapping fibers are effective to move moisture, essentially in one direction away from the body, in the finally formed product.

BRIEF DESCRIPTION OF THE DRAWINGS

Other objects, features and advantages of the invention will be apparent from the following description and from the drawing, wherein like reference characters in the respective drawn figures indicate corresponding parts. In the drawing.

DESCRIPTION OF THE PREFERRED EMBODIMENTS

Figure 1:
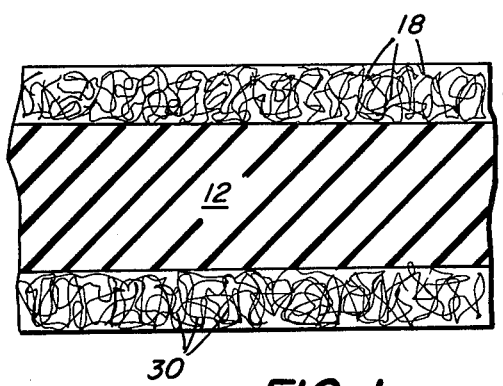
FIG. 1 is a schematic cross-section of a first stage in the preparation of the material of the invention, showing three layers of material.
Figure 2:
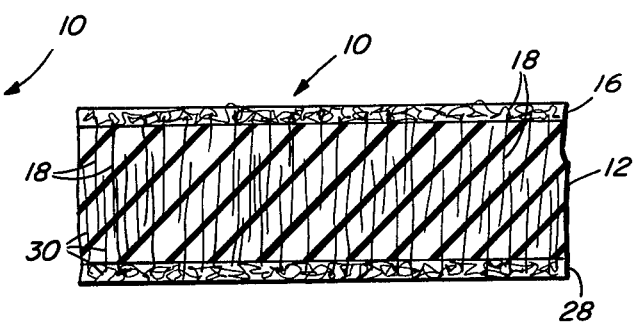
FIG. 2 is a schematic cross-section of the material of FIG. 1, after the inner and outer layers are needled into the middle layer.
Figure 3:
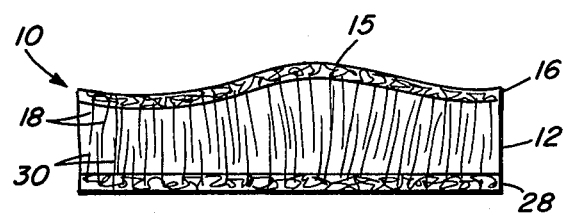
FIG. 3 is a schematic cross-section of the material of FIG. 2 after thermoforming to produce a pad.

As shown in FIGS. 1-3, the material 10 illustrating the invention has at least three layers. The middle layer 12 comprises a sheet of a closed-cell foamed thermoformable plastic. The top layer 16 is a non-woven mat of discrete hydrophobic fibers 18 such as polyester or polypropylene fibers, and the bottom layer 28 is a non-woven mat of discrete hydrophilic fibers 30 such as cotton.

Layer 12 may comprise any one of a number of known thermoformable plastic foam materials or blends thereof. Examples include materials such as polyethylene, ethylene vinyl acetate copolymers, crosslinked polyethylene, ploypropylene, polyacrylics, polyvinyl chloride, polystyrene, and the like. Such foamed, preformed thermoplastic sheet materials are available commercially. The moldable foam plastic layer 12 is selected to achieve the combination of properties best suited for the particular end use of the product. For example, relatively rigid foams such as cross-linked polyethylene closed-cell foam blown with nitrogen and sold under the trademark Plastozote are suitable for making body-fitting soft casts and shock absorbing pads. More flexible foams which provide cushioned support such as Evazote, a cross-linked copolymer of ethylene vinyl acetate and polyethylene blown with nitrogen, is well suited for fabricating innersoles. Various foams suitable for these and other purposes are also available, for example, from Voltek, Inc. Dynamit Nobel, or The Dow Chemical Company.

All of the foam plastic materials useful in the invention are thermoformable. Thus, after heating in an oven or by other means they are softened and can be permanently deformed but in the absence of applied force retain their shape and foam structure. Such materials may be molded or thermoformed in a mold cavity by, for example, compression molding or vacuum forming. Alternatively, in the case of certain materials such as the high quality nitrogen blown polyethylene and ethylene vinyl acetate materials sold under the trademarks Plastozote and Evazote, thermoforming can be conducted either in a mold cavity or directly on an exposed surface of the body.

The top layer 16 comprises a multiplicity of hydrophobic fibers 18 such as polypropylene or polyester. Other hydrophobic fibers may be used. The length of the fibers depends upon the overall thickness of the article being manufactured. For articles which after molding have a thickness ranging from about one-eighth inch to about five-eighths inch, fibers on the order of one half inch long suffice. Longer fibers should be used on thicker products such as impact-absorbing pads. The fibers are preferably thin, e.g., 10 microns in diameter or less, and are used at a density, for example, on the order of 2-10 ounces per square yaard of foam plastic, preferably about 6 ounces per square yard. Such hydrophobic fibers are known to have the ability to wick perspiration away from the body along the axis of the fiber.

The bottom layer 28 comprises a multiplicity of hydrophilic fibers 30 such as rayon or cotton fibers. The layer 28 is located adjacent the bottom of the foamed plastic layer 12, opposite the hydrophobic layer 16, and like layer 16, preferably comprises a non-woven mat of individual fibers needled into foam layer 12.

As is schematically shown in FIG. 1, in the manufacturing process of the invention the hydrophobic fibers 18 are scattered randomly about the upper surface of the thermoplastic foam layer 12 to form an intermingled fiber mat. The top layer 16 is formed and joined to layer 12 during the needling process wherein the fibers are threaded into the foam layer 12. As shown in FIG. 2, the fibers 18 are locked together to form a soft but sturdy top layer 16 comprising a substantially continuous nonwoven layer defining a multiplicity of interstitial spaces which in use tend to trap air. The needling procedure, by punching holes and imbedding water-transporting fibers downward into the thermoformable foam layer 12, allows moisture at the top layer 16 to be wicked into the interior of the foam layer 12. Similarly, during manufacture layer 28 originally takes the form of a mat of unwoven hydrophilic fibers 30, which are needled into the bottom surface of foam plastic layer 12 (see FIG. 2) and at least in part overlap the vertical extent of hydrophilic fibers 18, and form a non-woven fiber layer 28.

The laminate 10 shown in FIG. 2 may then be thermoformed into a desired shape conforming to a surface region of the body. Thermoforming is conducted by heating the needled material to a temperature sufficient to soften layer 12 without softening fibers 18 or 30 and without melting the plastic matrix of the foam or destroying its foam structure. The precise temperature employed depends upon the particular type of foam plastic material involved.

Figure 4:
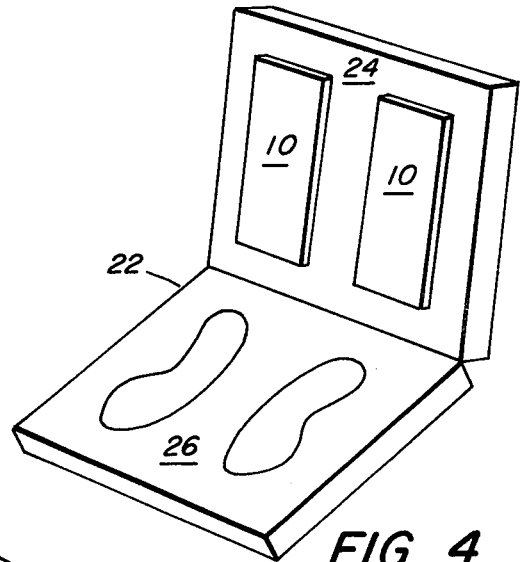
FIG. 4 shows blanks of the material of FIG. 2 in a mold prior to molding innersoles.
Figure 5:
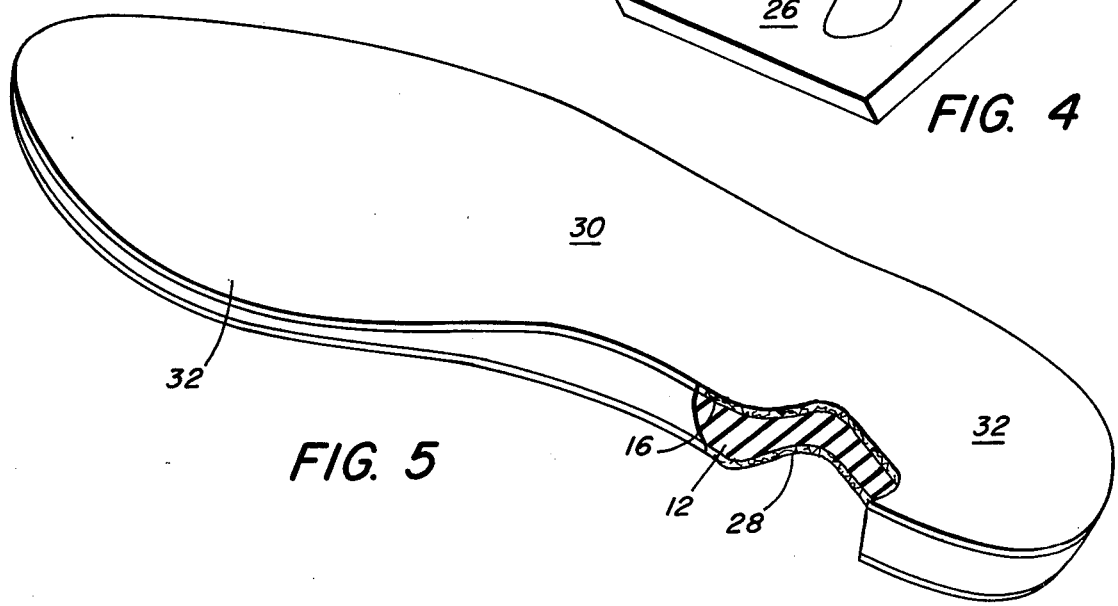
FIG. 5 illustrates an innersole, partly in cross-section, embodying the invention.

As illustrated in FIG. 4, thermoforming may be done in a cooled mold 22 by bringing the upper half 24 and the lower half 26 together on the preheated blanks 10. With a suitable mold, this action can convert the cross-section shown in FIG. 2 to the cross-section shown in FIG. 3, or can produce innersoles as illustrated in FIG. 5 or other products. As indicated generally in FIG. 3, heating the laminate 10 reduces the thickness of layer 12. Heating also relieves internal stress. Compression exerted by the mold will lock any fibers 18 and 30 penetrating the foam layer 12 in place by compressing the plastic foam. Upwardly facing surface 15 of layer 12 conforms to the mold shape. Layer 16 in turn conform substantially to the shape of surface 15.

The hydrophilic third layer 28 assists the moisture dispersion of the product that is initiated by the hydrophobic first layer 16. Thus, moisture's travel from the body is initiated by the wicking action of the hydrophobic fiber. The passage of the moisture into the ordinarily moisture impermeable foam layer 12 is facilitated by the openings created by the needling process. The overlap of the fibers permits moisture to be transferred within the foam from the hydrophobic wicking fibers to the absorbent hydrophilic fibers. Finally, the hydrophilic layer 28 enhances the passage of moisture by absorption and permits subsequent evaporation from surface 28 if in use it is exposed to the atmosphere. Penetration of moisture in the opposite direction is substantially absent.

The material of FIG. 3 may be molded in ways other than that illustrated in FIG. 4. One example is that certain foamed thermoplastics such as the cross-linked, nitrogen-blown polyethylene sold under the trademark Plastozote may after heating be pressed directly onto and shaped about an exposed part of the body such as a knee, ankle, or forearm without burning the skin or inducing severe discomfort. Laminate-like structures made with such materials in accordance with the invention make excellent soft casts and splints that remove perspiration and moisture from the body.

Thus the invention provides a material with superior moisture wicking capability that is comfortable in prolonged contact with the skin. Its needle-punched structure enhances the dispersion of perspiration. The needling and subsequent heating also relieve stress and cause the foam layer 12 to shrink slightly thereby locking the fiber in place. The material accordingly can withstand rough use. Furthermore, unlike moisture wicking structures of the prior art, the laminate of the invention may be shaped readily to conform to a surface region of the body on which it will be used. By selection of the foam, it is possible to provide a rigid cushioned support for a body part, to provide impact absorption capability, or to provide thermal insulation capability as desired. Casts and pads made in accordance with the invention help eliminate perspiration problems traditionally encountered with such products, and are comfortable in direct contact with the skin.

A molded resiliently supportive, moisture wicking innersole for use in footwear generally, but particularly in athletic footwear, is shown in FIG. 5 of the drawing. This product 32 includes an arch support section 30 and a heel cup section 32. Layers 12, 16 and 28, shown in cross-section, are constructed in accordance with the foregoing disclosure. The molded innersole thus produced is strong and durable enough to be incorporated directly into the sole of a shoe during its manufacture, or may be removable to facilitate repeated washings.

The invention may be embodied in other specific forms without departing from the spirit and scope thereof. Accordingly, other embodiments are within the following claims

What is claimed is:

1. A laminate-like structure having a surface conforming substantially to the contours of a surface region of the human body, the structure comprising:
    a foamed thermoplastic middle layer having a thermoformed surface conforming to the contours of said body surface region;
    a upper layer disposed on said thermoformed surface, comprising a multiplicity of hydrophobic fibers, a substantial fraction of which penetrate said middle layer, said fibers together comprising a non-woven, substantially continuous layer affixed to said middle layer and defining a multiplicity of interstitial spaces; and
    a lower layer disposed on the surface of said middle layer opposite said thermoformed surface, and comprising a multiplicity of hydrophilic fibers, a substantial fraction of which penetrate said middle layer and overlap with said hydrophobic fibers,
    said layers being effective to cooperate in use to maintain fibers of said upper layer in contact with perspiration from said body surface, and to wick perspiration away from said body surface and through said middle layer.

2. The structure of claim 1 comprising an innersole wherein said thermoformed surface conforms substantially to a portion of the sole of the human foot and includes an arch support section.

3. The structure of claim 2 wherein said innersole further includes a heel cup section.

4. The structure of claim 1 comprising means for immobilizing a region of the human body.

5. The structure of claim 1 comprising an impact-absorbing pad.

6. The structure of claim 1 wherein said foamed thermoplastic is selected from the group consisting of thermoformable polyetheylene, polypropylene, ethylene-vinyl acetate copolymers, cross-linked polyethylene, and mixtures thereof.

7. The structure of claim 1 wherein said fibers of said upper layer comprise a polymer selected from the group consisting of polypropylenes and polyesters.

8. The structure of claim 1 wherein said foamed thermoplastic comprises a closed-cell foam.

9. A method of forming an article of manufacture having a surface conforming substantially to the contours of a surface region of the human body for wicking perspiration away from said surface region, said method comprising the steps of:
    A. placing a multiplicity of hydrophobic fibers on a surface of a foamed thermoformable sheet;
    B. needle-punching said hydrophobic fibers into said thermoformable sheet to produce a non-woven, substantially continuous, fiber layer affixed to said thermoformable sheet;
    C. placing a multiplicity of hydrophilic fibers on a second surface of said thermoformable sheet opposite said first surface;
    D. needle-punching said hydrophilic fibers into said thermoformable sheet to a depth sufficient to overlap said hydrophobic fibers therewithin and to produce a non-woven, substantially continuous, fiber layer affixed to said thermoformable sheet;
    E. heating the product of step D to soften said thermoformable sheet; and
    F. imposing a surface contour to at least the side of said laminate comprising said hydrophobic fiber layer, said surface contour substantially conforming to said body surface region.

10. The method of claim 9 wherein steps E and F are effected by compression molding or vacuum molding.

11. The method of claim 9 wherein said thermoformable sheet comprises a polymer selected from the group consisting of polyethylene, polypropylene, ethylene-vinyl acetate copolymers, cross-linked polyethylene, and mixtures thereof.

12. The method of claim 9 wherein said hydrophobic fibers comprise a polymer selected from the group consisting of polypropylenes and polyesters.

13. A laminate-like structure for use in the production of thermoformed articles for placement in close proximity to the body, said laminate comprising:
    a thermoformable, closed-cell, foamed thermoplastic middle layer;
    an upper layer disposed on a first surface of said thermoplastic middle layer, comprising a multiplicity of hydrophobic fibers, a substantial fraction of which penetrate said middle layer, said fibers together comprising a soft, non-woven, substantially continuous layer affixed to said middle layer and defining a multiplicity of interstitial spaces; and
    a lower layer disposed on a second surface of said thermoplastic middle layer opposite said first surface, comprising a multiplicity of hydrophilic fibers, a substantial fraction of which penetrate said middle layer and overlap with said hydrophobic fibers.

14. The laminate of claim 13 wherein said first layer comprises a polymer selected from the group consisting of polyethylene, polypropylene, ethylene-vinyl acetate copolymers, cross-linked polyethylene, and mixtures thereof.

15. The laminate of claim 13 wherein said hydrophobic fibers comprise a polymer selected from the group consisting of polypropylene and polyester.

* * * * *